United States Patent [19]

Bigi et al.

[11] Patent Number: 4,739,062

[45] Date of Patent: Apr. 19, 1988

[54] METHOD OF PRODUCING PARAQUINONES

[75] Inventors: Franca Bigi; Giovanni Casiraghi; Giuseppe Casnati, all of Parma; Giovanni Sartori, Casalmaggiore, all of Italy

[73] Assignee: Consiglio Nazionale Delle Ricerche, Rome, Italy

[21] Appl. No.: 879,474

[22] Filed: Jun. 27, 1986

[30] Foreign Application Priority Data

Jul. 9, 1985 [IT] Italy ................................ 21494 A/85

[51] Int. Cl.[4] ...................... C07C 50/16; C07C 50/22; C07D 221/18; C07D 335/04
[52] U.S. Cl. ........................................ 546/77; 546/78; 546/101; 546/108; 548/421; 548/427; 549/24; 549/26; 549/388; 549/389; 260/351; 260/351.5; 260/365; 260/369; 260/383; 260/396
[58] Field of Search ............ 260/365, 351, 369, 351.5, 260/383, 396; 546/77, 78, 101, 108; 548/421, 427; 549/24, 26, 42, 44, 388, 389

[56] References Cited

U.S. PATENT DOCUMENTS 3,835,167 9/1974 Pfister ................................. 260/351
4,312,811 1/1982 Schoemans et al. ................ 260/369
4,393,221 7/1983 Broadhurst et al. .............. 260/351.5

OTHER PUBLICATIONS

Kerdesky et al, *Journal of Amer. Chem. Soc.*, vol. 110, No. 11, p. 3635, 1978, "A General, Selective & Facile Method for Ketone Synthesis from Acid Chlorides & Organotin Comp. Catalyzed by Pd".

Karsten Krohn, "Total Synthesis of Anthracyclinone" Angew. Chem. Int. Ed. Engl. 25 (1986) 790–807.

Russell, et al. "A Caveat Regarding Chiroptical Measurements of Chiral Anthracyclinones" Tetrahedron Letters, 25 No. 50 p. 5817 (1984).

Kimball, et al. "Anthracyclines and Related Substances, 4, A Novel Regio- and Stereoselective Total Synthesis of 7-Epidaunomycinone and Daunomycinone" Tetrahedron Letters, vol. 23, No. 38, pp. 3871–3874 (1982).

Kim, et al. "Anthracyclines and Related Substances I, A New Freidel-Crafts Alkylation Reaction Using 3—Bromophthalides, Efficient Synthesis of Islandicin, " Tetrahedron Letters No. 4, pp. 331–334, (1979).

*Primary Examiner*—Richard L. Raymond
*Assistant Examiner*—Raymond Covington
*Attorney, Agent, or Firm*—Bucknam and Archer

[57] ABSTRACT

A new widely-applicable method has been found for synthesis of 9,10-anthraquinones and similar chemical compounds of wide use in industry and pharmacology, by reacting suitable aromatic substrates with activated dicarboxylic acids (more particularly dichlorides) in the presence of metal halides. The special characteristics of the reaction are the good yields, high selectivity, the possibility of operating in a single reactor and the use of starting compounds which are cheap and easily available on the market.

8 Claims, No Drawings

METHOD OF PRODUCING PARAQUINONES

The invention relates to a method of preparing paraquinones and related compounds having the general formula I

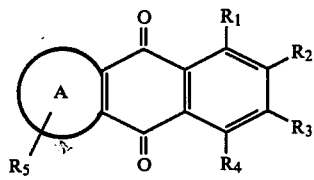

in which A represents an aromatic ring or an heteroaromatic ring having 5-6 members whereas $R_1$, $R_2$, $R_3$, $R_4$ or $R_5$, which can be the same or different from one another, each represent a hydrogen atom or an alkyl, aryl, hydroxyl, alkoxyl or nitro group; also $R_1+R_2$ or $R_2+R_3$ or $R_3+R_4$ can form an additional cyclic system, partially or totally unsaturated and orthocondensed on the benzene ring, derived from hydroquinones or other aromatic compounds, and from activated bicarboxylic acids, preferably in the form of dichlorides.

More particularly the invention relates to the preparation, in one step and of wide applicability, of 9,10 anthraquinones and similar compounds by reacting suitable hydroquinones (or other aromatic substrates) having at least positions 2, 3 free, with dicarboxylic acid dichlorides in the presence of a catalyst comprising a metal halide in a solvent of medium polarity.

The resulting paraquinones have varied, interesting applications. The most important use of anthraquinone is in the production of intermediates for the preparation of dye pigments—see Kirk-Othmer—*Encyclopedia of Chemical Technology*, vol. 8, p. 212-279—John Wiley and Sons—N.Y. 1979.

Anthraquinone is also used in the process of isomerization of vegetable oils (V. Sarzf, Indian J. Appl. Chem. 22, 146 (1909)) and as an accelerator in electrochemical processes (S. Katz, Brit. Pat. 1 029 686 (General Motors Corp.)).

Alkyl anthraquinones are used in the production cycle for hydrogen peroxide (W. S. Schumb, *Hydrogen Peroxide*, ACS Monograph No. 128, Reinhold Publishing Corp., 1955, p. 77).

Aminoanthraquinones are used in the synthesis of dye pigments and act as stabilizers of photodegradable polystyrene resins (K. Nakamura, Kobunshi, Ronbushu 31 373 (1974); Chem. Abstr. 81 1365804 (1974)).

Hydroxyanthraquinones are widely used in the preparation of dye pigments and as anti-oxidizing agents for lubricating oils (F. Oberender, Germ. Pat. No. 2 230 754 (Jan. 25, 1973) (Texaco Development Cor.)).

One special class of hydroxylated anthraquinones comprises variously substituted 1,4-dihydroxy-9,10-anthraquinones which represent the basic structure of anti-tumour anthracyclines. (F. Arcamone, *Doxorubicin Anticancer Antibiotics*, Medicinal Chemistry, Academic Press, 1981; S. Penco, *La Chimica e l'Industria*, V. 65, No. 5, 359 (1983)).

The methods hitherto used for synthesizing 9,10-anthraquinones are based on four fundamental processes. The first comprises oxidation of anthracenes with various oxidizing agents such as bichromates, nitric acid, chlorine, molecular oxygen and ozone (T. James, U.S. Pat. No. 2,865,933 (Koppers, Co.); L. Mahoney, U.S. Pat. No. 3,458,538 (Ford Motor Co.); L. Hutchings, U.S. Pat. No. 3,510,498 (Great Lakes Carbon Corp.); Calderazzo U.S. Pat. No. 3,642,838 (American Cyanamid Co.); H. Yasui, Japn. Kokai, 75 108 254 (Nippon Steel Chemical Co.); Ital. Pat. No. 869 293 (A.C.N.A. Sp.a.)).

The second method is based on acylation of benzene with phthalic anhydride in the presence of aluminium chloride to obtain orthobenzoyl benzoic acid which, in a second step is cyclized to anthraquinone in a medium comprising a protic acid such as conc. sulphuric acid, polyphosphoric acid or hydrofluoric acid (H. Stone, U.S. Pat. No. 1,656,575 (E. C. Klipstein and Sons Co.)).

Anthraquinone can also be synthesized by a Diels-Alder reaction between 1,4-naphthoquinone and 1,3-butadiene at 100°-110° C. in an autoclave, followed by oxidation in air of the resulting tetrahydroanthraquinone (K. Sakuma, Ger. OLS. No. 2 460 922 (Nippon Stec. Chemical Co.)).

A recently-reported novel method of preparing 9,10-anthraquinone is based on oxidation of indane obtained by dimerization of styrene (H. Armbrust, U.S. Pat. No. 3,764,631 (Badische Aniline und Soda Fabrik); H. Armbrust, U.S. Pat. No. 3,714,240 (Badische Aniline und Soda Fabrik); H. Engelbach, Ger. No. 2 314 695 (BASF).

Synthesis via phthalic anhydride can also be used in the preparation of 2-alkyl anthraquinones, but the drastic operating conditions (high temperature and extremely acid media) make regiochemical control more difficult and result in isomerization when using aromatics containing long chains of carbon atoms (C. A. Thomas, Anhydrous Aluminium Chloride in Organic Chemstry, A.C.S. Monograph No. 87, Reinhold Publishing Corp., N.Y. 1941).

Methyl anthraquinones can also be prepared from 1,4-naphthoquinones and methyl butadiene by the Diels-Alder reaction (H. Koehl, Ger. Pat. No. 2 162 949 (BASF).

Various hydroxy anthraquinones are prepared by the phthalic method using the Diels-Alder reaction (F. Arcamone, Doxorubicin Anticancer Antibiotics, Medicinal Chemistry, Academic Press, 1981; S. Penco, La Chimica e l'Industria, 65, 359 (1983)).

However the aforementioned methods have serious limitations, mainly because the reaction conditions, which are usually drastic, make it impossible to obtain economic yields of paraquinones containing substituent groups which, under the aforementioned reaction conditions, undergo isomerization or racemization even when there is no pronounced degradation of the final products.

The object of the invention therefore is to provide a method of producing paraquinones and related compounds, the method being widely applicable, direct and relatively simple and gentle and characterised by good yields, high selectivity, regiochemical and stereochemical control, and using catalysts and solvents which are economic and easily available on the market.

These and other aims which will be clearer to one skilled in this field, are obtained according to the invention by means of a method of synthesizing paraquinones I characterised in that activated dicarboxylic acids, preferably in the form of acyl dichlorides II

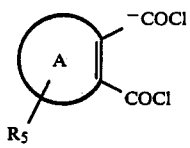

where A and $R_5$ have the meanings given previously, are reacted with an aromatic substrate having the general formula III

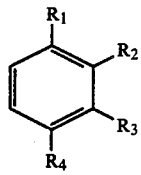

where $R^1$, $R^2$, $R^3$ and $R^4$ have the meanings given previously, in substantially stoichiometric proportions at a temperature between 80° and 120° C., preferably about 100° C., in the presence of a metal halide chosen from among halides of metals in group III or IV of the periodic table or transition metals, preferably anhydrous aluminium chloride or bromide, in the proportion of 2-3 mol equivalents relative to the aromatic compound III, in a moderately polar medium such as nitrobenzene, nitromethane or tetrachloroethylene.

The concentrations of species III in the solvent are not critical and can vary between about 5 and 30% by weight. The result, according to the present method, is selective direct synthesis of paraquinones via an (apparent) bisacylation of two carbon atoms adjacent the aromatic ring with minimum production of counteracting oxygen products.

The following solvents have been found effective: aprotic, moderately polar compounds such as nitro derivatives (nitrobenzene, nitromethane), and polyhalogenated hydrocarbons (tetrachloroethylene).

The reaction times vary with the operating temperatures and the reactivity of the chosen products; in practice at 100° C., times between 10 minutes and 1 hour are sufficient for completing the process. To obtain higher efficiency, it is advisable to agitate the reacting substance. It is also stressed that the operating conditions for the entire process are particularly gentle and that the reaction proceeds with total maintenance of chirality when optically active reagents are used.

In a particularly preferred embodiment, the process according to the invention is carried out by first dissolving the Lewis acid (in the proportion of approx. 2-3 mols per mol of aromatic substrate III) in the solvent, adding substrate III, also dissolved in the same solvent if necessary, to the solution, and heating the entire mixture to a temperature of the order of 100° C. After about 5-20 minutes of agitation at this temperature, the dichloride II is gradually added, dissolved in the same solvent, at a speed such as to maintain the temperature at around 100° C. without further external heating. When addition is complete, agitation is continued at the same temperature for about 30 minutes, the mixture is left to cool at ambient temperature, and is inactivated with an excess of saturated aqueous solution oxalic acid. The mixture is extracted a number of times with diethyl ether and the combined extracts are dried over anhydrous $Na_2SO_4$.

The solvent is evaporated at reduced pressure, giving the crude product which is separated from unconsumed starting compounds by crystallization from suitable solvents or by normal chromatography on silica.

As already stated, the concentrations are not critical. In the preferred procedure described hereinbefore the concentration of the initial solution of Lewis acid (e.g. $AlCl_3$) in the solvent (e.g. nitrobenzene) can vary from 5 to 10% by weight/volume; the concentration of aromatic substrate III and dichloride II can vary from 10 to 30% by weight/volume.

As already mentioned, the known formation of anthraquinones from orthobenzoylbenzoic acid occurs only under drastic conditions, using strongly proton-accepting agents. Kinetic studies of the behaviour of orthobenzoylbenzoic acid in the presence of these agents has resulted in the formulation of a mechanism which can be summarised as follows:

REACTION SCHEME 1

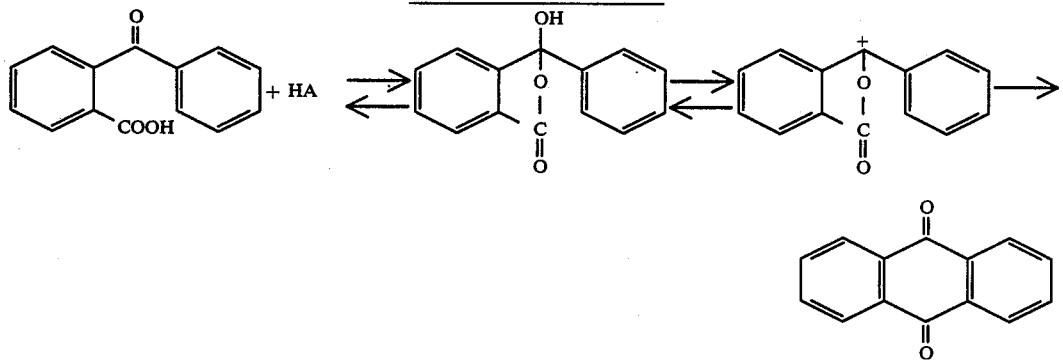

where HA is hydrofluoric, polyphosphoric or sulphuric acid; see M. S. Newman et al., *J. Am. Chem. Soc.* 67, 704 (1945); R. J. Downing et al., ibid. 84, 4956 (1962); D. S. Noyce et al., *J. Org. Chem.* 30, 1896, (1965).

The surprising feature of the invention, as already stated, is the special gentleness of the reaction conditions, with all the advantages of regiospecificity and the resulting retention of chirality. These advantages are absent when using known methods of obtaining anthraquinones and similar substances.

On the basis of the experimental results, the reaction claimed here may be interpreted by assuming the formation of reactive intermediate IV:

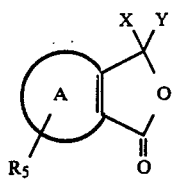 (IV)

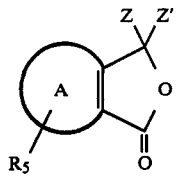 (V)

(where A and $R_5$ have the meanings given previously whereas X denotes halogen, alkoxyl and aryloxyl and Y denotes halogen, alkoxyl or aryl), the intermediates originating from (a) transposition of mono-acylation products similar to that assumed in Diagram 1, or (b) the reaction between aromatic substrates III and dichlorophthalides or dialkoxyphthalides having the formula V (where A and $R_5$ have the meanings given previously whereas Z and Z', which are the same as one another, represent chlorine or alkoxyl). Reactions (a) and (b) are illustrated by diagram 2, which by way of example uses two specific starting compounds, i.e. phthalic acid dichloride (or the corresponding dichlorophthalide, see A. Kirpel et al., Ber. 68, 1330 (1935)), and 1,4-dimethoxybenzene.

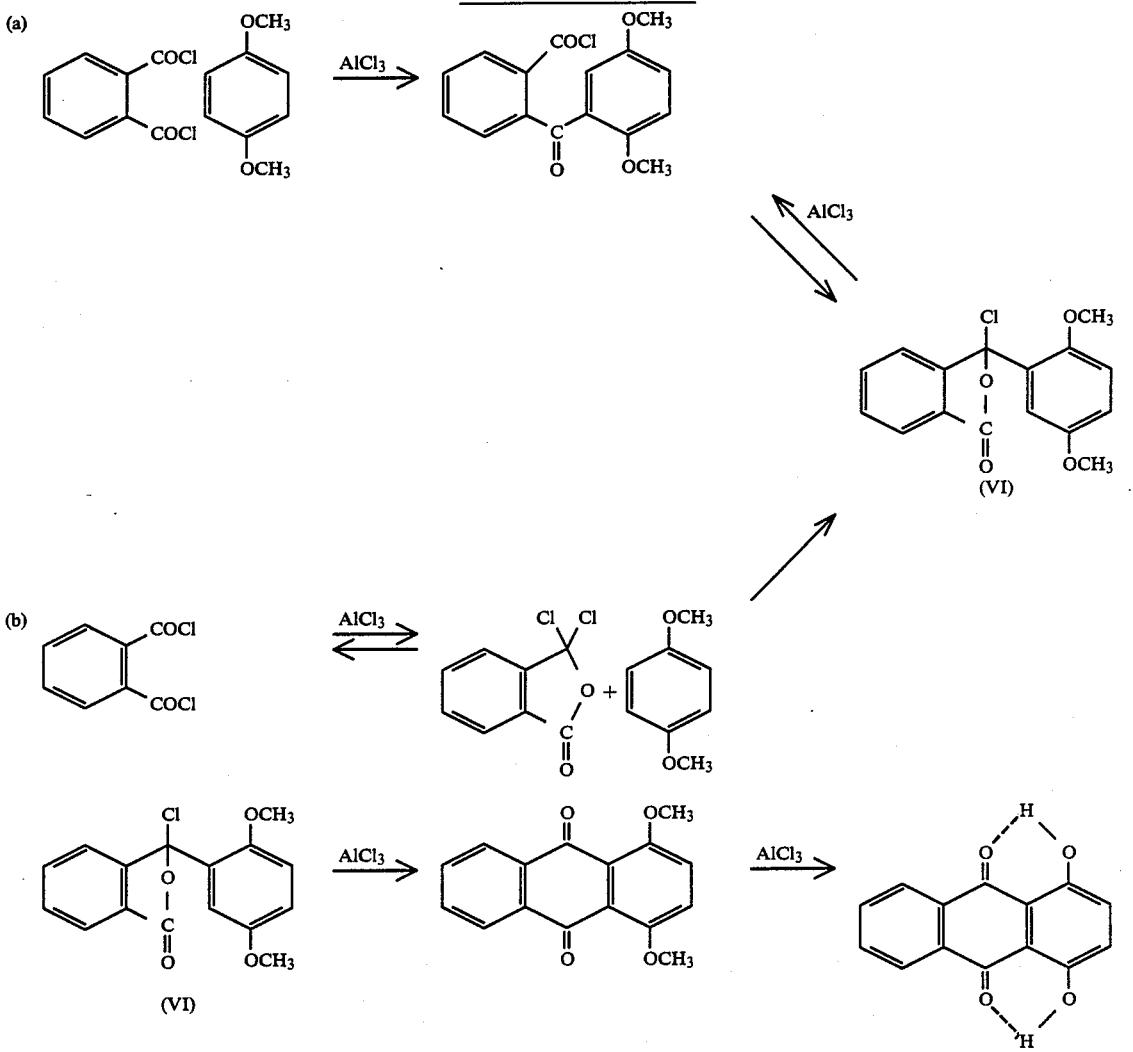

REACTION SCHEME 2

Intermediate VI could not be isolated, but Diagram 2 is confirmed by the fact that if, other conditions being equal, the reaction between phthalic acid dichloride and 1,4-dimethoxybenzene is carried out at low temperature (25° C.) and for short periods (5 minutes), no anthraquinone products are obtained but two compounds which have been assigned structures VII and VIII are isolated:

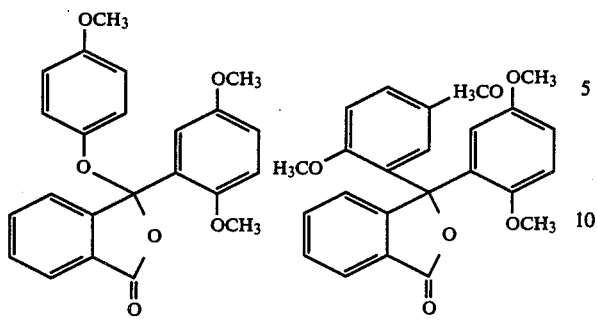

The formation of compound VII (1-(4-methoxyphenoxy)-1-(2,5-dimethoxyphenyl)-isobenzofuranone-3) may be attributed to the reaction between chlorophthalide VI and oxygen in a methoxyl group, the formation of compound VIII (1,1-di-2,5-dimethoxyphenyl)-isobenzofuranone-3) may be attributed to reaction between the aforementioned chlorophthalide and a nuclear carbon atom of dimethoxybenzene. If VII is heated under the conditions of the present process, the product is a quantitative yield of 1,4-dihydroxy-9,10 anthraquinone, via intramolecular acylation assisted by the breakage of a C—O bond and the consequent detachment of a good ending group (p-methoxyphenol). In the case of VIII it would be necessary to break a C—C bond, which is disadvantageous from the energy point of view. In practice, VIII cannot be converted into 1,4-dihydroxy-9,10-anthraquinone.

The invention therefore also covers a method of preparing paraquinones I from isolated type IV and V intermediates, and the invention covers intermediates of the same type when novel.

The invention will now be described in greater detail in the following examples, given by way of illustration only. The Table shows the structure of the products synthesized in the various examples.

TABLE

Structure of products obtained in the various examples.

| Example No. | Product |
|---|---|
| 1 | anthraquinone |
| 2 | 1,4-dihydroxyanthraquinone |
| 3 | 1,4-dihydroxy-2-methylanthraquinone |
| 4 | azaanthraquinone with 1,4-dihydroxy |
| 5 | nitro-substituted 1,4-dihydroxyanthraquinone |
| 6 | dioxolo-fused 1,4-dihydroxyanthraquinone |
| 7 | dioxolo-fused 1,4-dihydroxy-2-methylanthraquinone |
| 8 | 1,2-dihydroxyanthraquinone |
| 9 | 5,12-dihydroxy-1,2,3,4-tetrahydronaphthacenequinone |
| 10 | 6,11-dihydroxynaphthacene-5,12-dione |
| 11 | benz[a]anthracene-7,12-dione |

TABLE-continued

Structure of products obtained in the various examples.

| Example No. | Product |
|---|---|
| 12 | (structure: tetracyclic quinone with OH, OH, CH3, OH substituents — 9,10-anthraquinone fused with a cyclohexane ring bearing OH and COCH3 groups, with two phenolic OH groups) |
| 13 | (structure: 2-methoxy-9,10-anthraquinone) |

EXAMPLE 1

7.2 g (0.2 mols) of benzene were added at ambient temperature and in a gentle stream of dry nitrogen to 26.6 g (0.2 mols) of anhydrous $AlCl_3$ in 300 ml nitrobenzene. The mixture was heated to 100° C.; after agitation for 15 minutes at this temperature, 20.2 g (0.1 mols) of phthalic acid dichloride dissolved in 100 ml nitrobenzene were added during about 20 minutes. The volume of the solution was made up to 500 ml with nitrobenzene and the temperature was kept at 100° C. with agitation for 30 minutes, after which the reacting substance was cooled and 300 ml of saturated aqueous solution of oxalic acid was added with intense agitation. Three extractions were made, each time with 200 ml ethyl ether and the combined extracts were dried over anhydrous $Na_2SO_4$. The solvent was removed under reduced pressure and the product was purified by crystallization from toluene, giving 17.7 g (85% yield) of 9,10-anthraquinone (1), m.p. 285° C. (literature: 286° C., EtOH).

EXAMPLE 2

The method was the same as in Example 1, but using 11.0 g (0.1 mols) of hydroquinone and 20.1 g (0.1 mols) of phthalic acid dichloride. The product was 15.6 g (65% yield) of 1,4-dihydroxy-9,10-anthraquinone (2), m.p.=199° C. (literature 200°–202° C. EtOH).

EXAMPLE 3

The method was the same as in Example 1 but using 12.4 g (0.1 mols) of 2-methyl hydroquinone and 20.2 g (0.1 mols) of phthalic acid dichloride. The product was 15.7 g (62% yield) of 2-methyl-1,4-dihydroxy-9,10-anthraquinone (3), m.p.=177°–178° C. (literature 178°–179° C. EtOH).

EXAMPLE 4

The method was the same as in Example 1, but using 11.0 g (0.1 mols) of hydroquinone and 20.3 g (0.1 mols) of 3,4-piridine-dicarboxylic acid dichloride. The product was 14.5 g (60% yield) of 6-aza-1,4-dihydroxy-9,10-anthraquinone (4), m.p.=174°–176° C. (EtOH). The compound had the following characteristics:

IR (KBr, cm$^{-1}$): 2918, 1722, 1618, 1441, 1259, 1211, 792, 761.

$^1$H-NMR (CDCl$_3$, δ): 7.38 (s, 2H, H-2 and H-3); 8.12 (d, 1H, H-8, J=5.0 Hz); 9.13 (d, 1H, H-7, J=5.0 Hz); 9.62 (s, 1H, H-5); 12.66 (s, 1H, OH); 12.79 (s, 1H, OH).

MASS (m/e, % relative intensity): 241 (100) 213 (10), 185 (9), 171 (9), 102 (12).

UV (EtOH): λ 206 230 259 (s) 296 463 (fl) 488 522 (s). ε 14580 17951 7749 5440 4065 4421 3174.

EXAMPLE 5

The method was similar to that in Example 1 but using 11.0 g (0.1 mols) of hydroquinone and 24.7 g (0.1 mols) of 4-nitrophthalic acid dichloride. The product was 21.4 g (75% yield) of 6-nitro-1,4-dihydroxy-9,10-anthraquinone (5), m.p.=226°–228° C. (EtOH). The compound had the following characteristics:

IR (KBr, cm$^{-1}$): 1625, 1598, 1528, 1440, 1330, 1238, 1205, 1145, 790, 762.

$^1$H-NMR (CDCl$_3$, δ): 7.42 (s. 2H, H-2 and H-3); 8.5–8.7 (m, 2H, H-7 and H-8); 9.16 (d, 1H, H-5, J=1.7 Hz); 12.75 (s, 1H, OH); 12.78 (s, 1H, OH).

MASS (m/e, % relative intensity): 285 (100), 255 (10), 239 (27); 227 (10), 211 (28), 183 (24), 127 (26).

UV (EtOH): λ 253 260 264 319 469 (fl) 495 530 (fl). ε 18104 18638 17745 2686 6140 6782 4254.

EXAMPLE 6

The method was similar to that in Example 1 but using 11.0 g (0.1 mols) of hydroquinone and 19.2 g (0.1 mols) of 3,4-furanedicarboxylic acid dichloride. The product, with a 40% yield, was 1,4-dihydroxy-c-furanonaphthoquinone (6), mp.=163°–165° C. The compound had the following characteristics:

IR (KBr, cm$^{-1}$): 3094, 2900, 1655, 1600, 1515, 1274, 1120, 857, 840.

$^1$H NMR (CDCl$_3$, δ): 7.28 (s, 2H, H-5 and H-7); 8.25 (s, 2H, H-2 and H-3); 12.79 (s, 2H, OH).

MASS (m/e % relative intensity): 230 (100), 184 (10), 147 (55), 122 (80), 107 (75).

UV (EtOH): λ 206 223 285 438 448 465 (a) 477 (s). ε 7858 8638 1814 2401 2382 1922 1491.

EXAMPLE 7

The method was the same as in Example 1 but using 12.4 g (0.1 mols) of 2-methyl-hydroquinone and 19.2 g (0.1 mols) of 3,4-furane-dicarboxylic acid dichloride. The product was 10.2 g (42% yield) of 2-methyl-1,4-dihydroxy-c-furanonaphthoquinone (7), m.p.=150°–151° C. The compound had the following characteristics:

IR (KBr, cm$^{-1}$): 3100, 2910, 1670, 1609, 1522, 1283, 1222, 1130, 864, 848.

$^1$H-NMR (CDCl$_3$, δ): 2.34 (d, 3H, Ar—CH$_3$, J=1,1 Hz); 7.54 (s, 2H, H-5 and H-7); 8.21 (d, 1H, H-3, J=1.1 Hz); 12.81 (s, 1H, OH); 13.20 (s, 1H, OH).

MASS (m/e, % relative intensity): 244 (50), 184 (10), 147 (100), 119 (38).

UV (EtOH): λ 207 248 (s) 254 (fl) 440 448 468 (S) 478 (s). ε 17492 7692 7571 2342 2428 1935 1500.

EXAMPLE 8

The method was similar to Example 1, using 11.0 g (0.1 mol) of 1,2-dihydroxybenzene and 20.2 g (0.1 mol) of phthalic acid dichloride. The product was 13.2 g (55% yield) of 1,2-dihydroxy-9,10-anthraquinone (8), m.p.=288°–289° C. (literature 288°–289° C. EtOH).

EXAMPLE 9

The method was similar to Example 1 but using 16.4 g (0.1 mols) of 1,4-dihydroxy-5,6,7,8-tetrahydronaphthalene and 20.2 g (0.1 mol) of phthalic acid dichloride. The product was 33.7 g (88% yield) of 6,11-dihydroxy-7,8,9,10-tetrahydro-5,12-naphtacenequinone (9), m.p.=194°–196° C. (EtOH).

EXAMPLE 10

The method was the same as in Example 1, using 16.0 g (0.1 mols) of naphthohydroquinone and 20.2 g (0.1 mols) of phthalic acid dichloride. The product was 15.9 g (55% yield) of 6,11-dihydroxy-5,12-naphtacenequinone (10), m.p.=214°–216° C. (EtOH.

EXAMPLE 11

The method was similar to Example 1, using 12.8 g (0.1 mols) of naphthalene and 20.2 g (0.1 mols) of phthalic acid dichloride. The product was 23.2 g (85% yield) of benzo/a/ anthracene-7,12-dione (11), m.p. 168°–170° C. (literature 169° C.)

EXAMPLE 12

The method was similar to Example 1, using 25.0 g (0.1 mols) of (−)-7-acetyl-7-oxy-1,4-dimethoxytetralene and 20.2 g (0.1 mols) of phthalic acid chloride. The product was 29.9 g (85% yield) of (−)-4-dimethoxy-7-deoxydaunomicinone (11), m.p. 210° C., /α/$_D^{20}$= −19° (c=0.09 g/100 ml di EtOH/CHCl$_3$ 1/1).

EXAMPLE 13

The method was similar to that in Example 1, using 10.8 g (0.1 mols) of anisole and 20.2 g (0.1 mols) of phthalic acid dichloride. The product was 19.0 g (60% yield) of 2-methoxy-9,10-anthraquinone (13), m.p. 195°–197° C.

EXAMPLE 14

(Isolation of Intermediates)

0.1 mols of 1,4-dimethoxybenzene dissolved in 100 ml nitrobenzene was added at ambient temperature to a solution of 0.2 mols AlCl$_3$ in 300 ml nitrobenzene, followed by 0.1 mols of phthalic acid dichloride, added rapidly at about 20° C. The mixture was agitated at 25° C. for 5 minutes, after which a saturated aqueous solution of oxalic acid was added immediately. After the usual extraction operations with ethyl ether an organic phase was obtained and dried over Na$_2$SO$_4$. The solvent was eliminated in vacuo; the residue was chromatographed over silica gel (eluent: hexane/ethyl acetate 1/1). Compounds VII and VIII were obtained with respective yields of 40% and 30% on dimethoxybenzene. Compound VII (mp.=392) was examined by mass spectroscopy with the followint results (m/e, relative intensity): 392 (15), 269 (10), 255 (8), 165 (6), 137 (5), 123 (5). As a result of treatment with AlCl$_3$ in nitrobenzene (100° C., 20 minutes) the substance was quantitatively converted into 1,4-dihydroxy-9,10-anthraquinone (2).

Compound VII (m.p.=406), proposed structure:

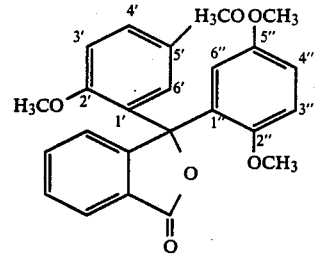

was found to have the following characteristics:

$^1$H NMR (CDCl$_3$, δ): 3.45 and 3.70 (12H, OCH$_3$); 6.85 (s. 4H, H-3', H-4', H-3", H-4"); 6.90 (s, 2H, H-6' and H-6"); 7.48 and 7.60 (2t, 2H, H-4 and H-5, J=9.0 Hz); 7.88 (d, 2H, H-3 and H-6, J=9.0 Hz).

MASS (m/e, % relative intensity): 406 (100), 375 (6), 347 (29), 331 (20), 269 (40), 239 (19), 211 (20).

We claim:

1. A method of preparing paraquinones of formula I

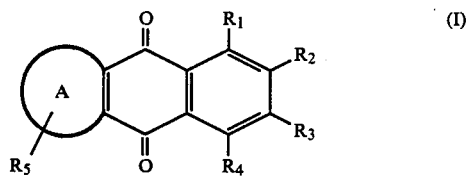

in which A is an aromatic ring or a hetero-aromatic 5–6 member ring and R$_1$, R$_2$, R$_3$, R$_4$ and R$_5$ are the same or different from one another and are hydrogen, alkyl, aryl, hydroxy, alkoxy or nitro; or R$_1$+R$_2$, or R$_2$+R$_3$ or R$_3$+R$_4$ form another ring, partly or totally unsaturated and orthocondensed on the benzene ring, which consists of reacting an aromatic substrate of formula III

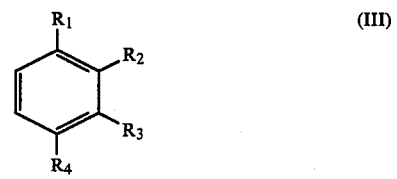

in which R$_1$, R$_2$, R$_3$ and R$_4$ are as defined hereinabove with a compound which is a dichloride of a carboxylic acid (II) or a phthalide of formula (IV)

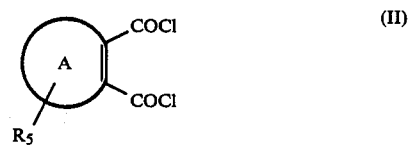

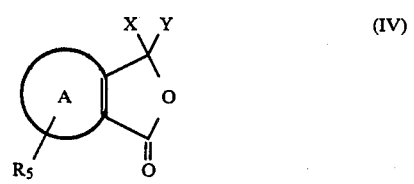

in which A and R$_5$ are as defined hereinabove and X is halogen, alkoxy or aryloxy and Y is halogen, alkoxy or aryl in the presence of an halide of a metal which is a mamber selected from the group consisting of metals of group III and IV of the periodic table and transition metals, in a moderately polar solvent at a temperature between 80° and 120° C.

2. The method according to claim 1, wherein the ratio of the aromatic substrate III to the reactive compound II or IV is substantially stoichiometric.

3. The method according to claim 1 wherein the metal halide is used in the propration of 2-3 mols per mol of aromatic substrate III.

4. The method according to claim 1, wherein the metal halide is anhydrous $AlCl_3$ or $AlBr_3$.

5. The method according to 1 wherein the solvent is nitrobenzene, nitromethane or tetrachloroethylene.

6. The method according to claim 1 wherein (a) The metal halide is first dissolved in the solvent;
(b) The aromatic substrate III, is added;
(c) The solution obtained in (b) is heated to about 100° C.;
(d) The reactive compound II or IV is gradually added at the same temperature, and
(e) At the end of the reaction the resulting mixture is treated with an excess of saturated aqueous solution of oxalic acid and the reaction products are isolated from the reaction mixture.

7. The metal as to claim 6 wherein said aromatic substrate III in step (b) is dissolved in said solvent.

8. The method according to claim 7 wherein said compound II or IV is dissolved in said solvent in step (d).

* * * * *